(12) United States Patent
Potter et al.

(10) Patent No.: US 10,488,372 B2
(45) Date of Patent: Nov. 26, 2019

(54) SYSTEMS AND METHODS FOR DETECTING DAMAGE IN ROTARY MACHINES

(71) Applicant: General Electric Company, Schenectady, NY (US)

(72) Inventors: Joshua Jeffrey Potter, Albany, NY (US); Jeremy Charles Canary, Peyton, CO (US)

(73) Assignee: General Electric Company, Schenectady, NY (US)

( * ) Notice: Subject to any disclaimer, the term of this patent is extended or adjusted under 35 U.S.C. 154(b) by 170 days.

(21) Appl. No.: 15/678,238

(22) Filed: Aug. 16, 2017

(65) Prior Publication Data
US 2019/0056358 A1   Feb. 21, 2019

(51) Int. Cl.
*G01N 29/12* (2006.01)
*G01N 29/48* (2006.01)
(Continued)

(52) U.S. Cl.
CPC ....... *G01N 29/4445* (2013.01); *F01D 21/003* (2013.01); *F03D 17/00* (2016.05);
(Continued)

(58) Field of Classification Search
CPC .... G01N 29/12; G01N 29/4445; G01N 29/48; G01N 2291/023; G01H 1/003;
(Continued)

(56) References Cited

U.S. PATENT DOCUMENTS 6,078,874 A * 6/2000 Piety ...................... G01H 1/003
702/122
8,171,797 B2   5/2012 Hatch et al.
(Continued)

FOREIGN PATENT DOCUMENTS

WO   2017/168226 A1   10/2017

OTHER PUBLICATIONS

Extended European Search Report and Opinion issued in connection with corresponding EP Application No. 18188411.5 dated Jan. 22, 2019.

*Primary Examiner* — Jacques M Saint Surin
(74) *Attorney, Agent, or Firm* — Dority & Manning, P.A.

(57) ABSTRACT

A method for detecting damage in a component of a rotary machine includes collecting, via one or more sensors, vibration data relating to the component. The method also includes identifying energy of at least one harmonic or sideband series within the at least one region indicative of a damaged component and identifying energy within the at least one region excluding the at least one harmonic or sideband series. Further, the method includes determining at least one damage ratio based on the energy of at least one harmonic or sideband series within the at least one region indicative of a damaged component and the energy within the at least one region excluding the at least one harmonic or sideband series. Moreover, the method includes calculating a damage factor of the component as a function of, at least, the at least one damage ratio. In addition, the method includes comparing the damage factor to a predetermined damage threshold, wherein a damage factor exceeding the predetermined damage threshold is indicative of a damaged component.

17 Claims, 8 Drawing Sheets

(51) Int. Cl.
*F01D 21/00* (2006.01)
*G01H 1/00* (2006.01)
*G01M 13/021* (2019.01)
*G01M 13/028* (2019.01)
*F03D 17/00* (2016.01)
*G01M 15/14* (2006.01)
*G01N 29/44* (2006.01)
*F03D 15/00* (2016.01)

(52) U.S. Cl.
CPC .......... *G01H 1/003* (2013.01); *G01M 13/021* (2013.01); *G01M 13/028* (2013.01); *G01N 29/12* (2013.01); *G01N 29/48* (2013.01); *F03D 15/00* (2016.05); *F05B 2270/334* (2013.01); *G01M 15/14* (2013.01); *G01N 2291/023* (2013.01)

(58) Field of Classification Search
CPC ........ F03D 17/00; F03D 15/00; F01D 21/003; G01M 15/14; G01M 13/021; G01M 13/028; F05B 2270/334

USPC .......................................................... 73/579
See application file for complete search history.

(56) References Cited

U.S. PATENT DOCUMENTS

| | | | |
|---|---|---|---|
| 2002/0169569 | A1 | 11/2002 | Miller |
| 2005/0171736 | A1* | 8/2005 | Kang .................... G01H 1/006 702/185 |
| 2008/0223135 | A1* | 9/2008 | Blanchard .......... G01M 13/045 73/579 |
| 2008/0234964 | A1* | 9/2008 | Miyasaka .............. G01H 1/003 702/113 |
| 2011/0071769 | A1* | 3/2011 | Akashi ................... G01N 25/72 702/35 |
| 2012/0065901 | A1 | 3/2012 | Bechhoefer et al. |
| 2014/0257714 | A1 | 9/2014 | Kiviniemi et al. |
| 2015/0276823 | A1* | 10/2015 | Rodriguez ........... G01R 31/343 702/75 |
| 2015/0355044 | A1 | 12/2015 | Cardinal et al. |
| 2017/0145852 | A1 | 5/2017 | McCune et al. |

* cited by examiner

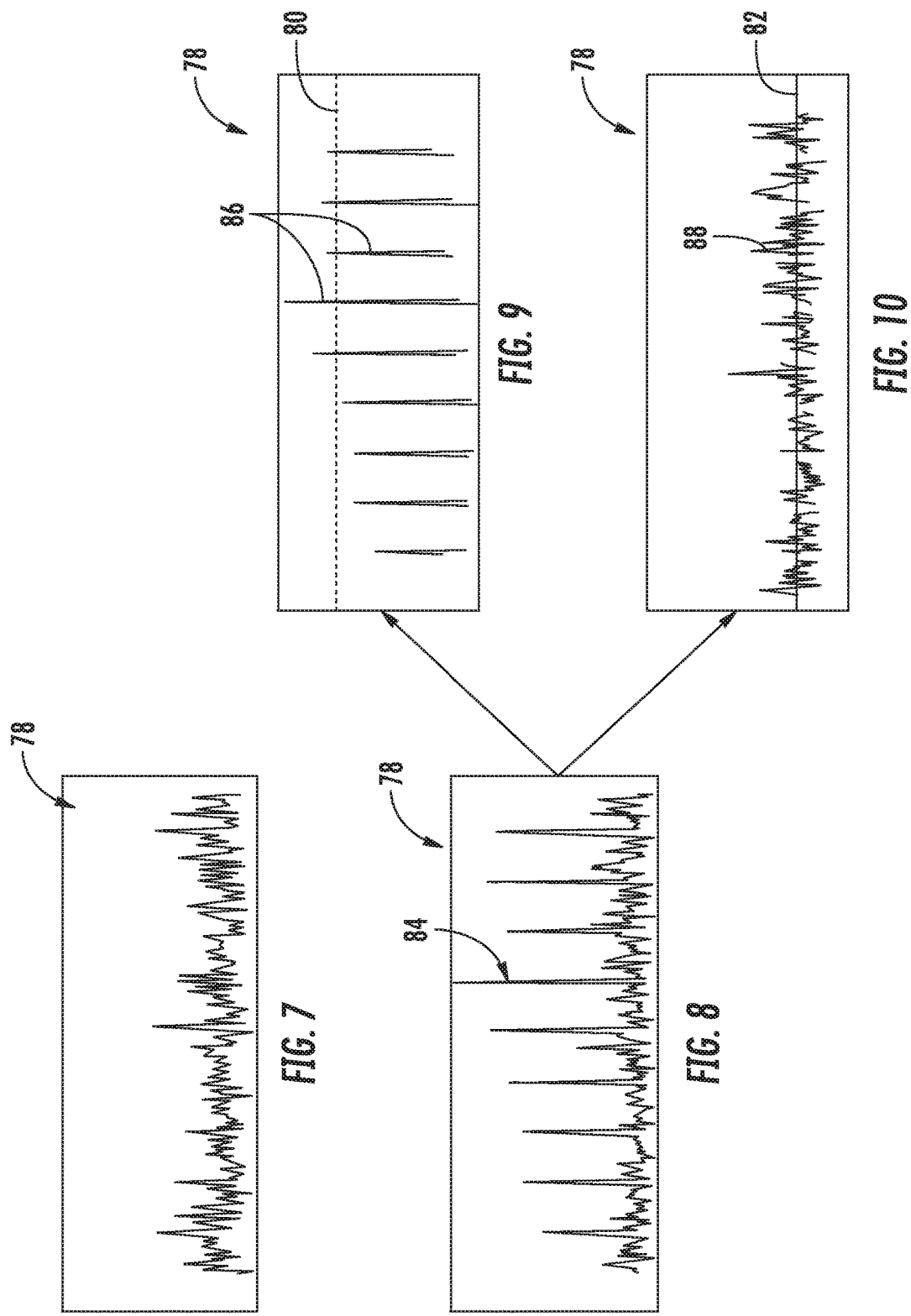

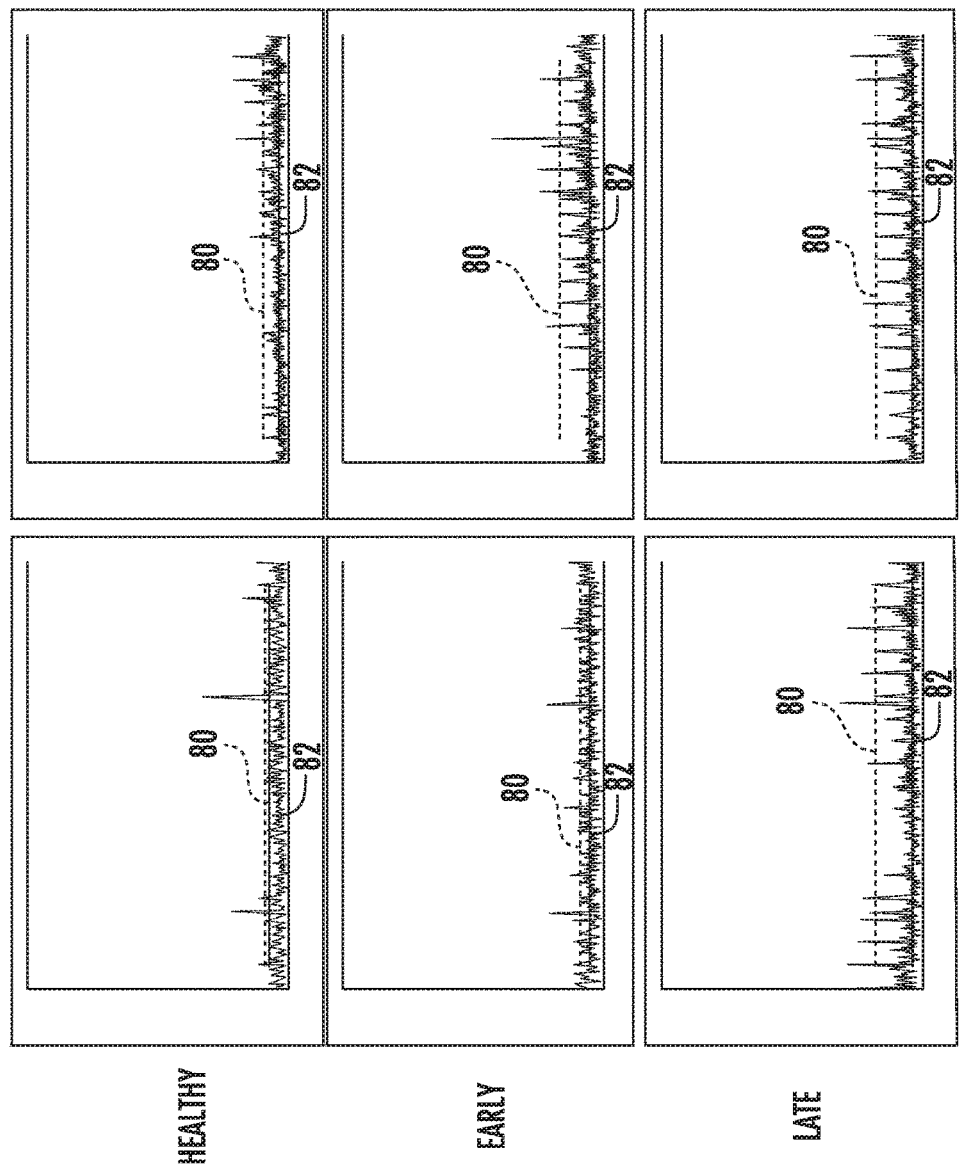

SYSTEMS AND METHODS FOR DETECTING DAMAGE IN ROTARY MACHINES

FIELD

The present disclosure relates in general to rotary machines, and more particularly to systems and methods for detecting damage in such rotary machines.

BACKGROUND

Wind power is considered one of the cleanest, most environmentally friendly energy sources presently available, and wind turbines have gained increased attention in this regard. A modern wind turbine typically includes a tower, a generator, a gearbox, a nacelle, and one or more rotor blades. The rotor blades capture kinetic energy of wind using known foil principles. The rotor blades transmit the kinetic energy in the form of rotational energy so as to turn a low-speed main shaft coupling the rotor blades to a gearbox, or if a gearbox is not used, directly to the generator. For example, the generator may be coupled to the low-speed main shaft such that rotation of the shaft drives the generator. For instance, the generator may include a high-speed generator shaft rotatably coupled to the main shaft through the gearbox. The generator then converts the mechanical energy from the rotor to electrical energy that may be deployed to a utility grid.

In addition, modern wind turbines include a plurality of high-speed and low-speed bearings to provide rotation of the various components thereof. For example, the low-speed main shaft typically includes one or more main bearings mounted at a forward and rearward end thereof to allow the low-speed main shaft to rotate about an axis. Further, the gearbox generally includes a gearbox housing containing a plurality of gears (e.g., planet, ring and/or sun gears) connected via one or more planetary carriers and bearings, in addition to parallel gears connected via shafts and bearings, for converting the low speed, high torque input of the rotor shaft to a high speed, low torque output for the generator.

Detection of damaged components in a wind turbine (or any rotary machine) is essential in minimizing unplanned downtime of the turbine and increasing turbine availability. Current detection algorithms for gearbox gear damage (specifically, the ring gear, planet gear, and low-speed intermediate stage gear) do not consistently trend gear damage energy with enough separation from healthy gears. Lack of separation in the trends from healthy to damaged gears results in missed diagnosis of failing components and increased probability of false positive events for healthy components. Visual detection of failing gear sideband and harmonic energy patterns has proven successful in locating damaged components; however, this approach relies on the consistent manual inspection of the spectrums. Such inspection is inherently time consuming and can result in missed detection of failed components. In addition, although manual inspection methods have been utilized with success, such methods do not provide a scalable option and result in reduced monitoring efficiency.

For at least the aforementioned reasons, the detection of component damage of rotary machines has proven difficult to automate using traditional detection analytics and/or trending techniques. Accordingly, improved systems and methods for detecting damage in such rotary machines would be desired in the art.

BRIEF DESCRIPTION

Aspects and advantages of the invention will be set forth in part in the following description, or may be obvious from the description, or may be learned through practice of the invention.

In one aspect, the present disclosure is directed to a method for detecting damage in a component of a rotary machine. The method includes collecting, via one or more sensors, vibration data relating to the component. The method also includes identifying at least one low-energy region within the vibration data. The method further includes identifying energy of at least one harmonic or sideband series within the at least one region indicative of a damaged component and identifying energy within the at least one region excluding the at least one harmonic or sideband series. Further, the method includes determining at least one damage ratio based on the energy of at least one harmonic or sideband series within the at least one region indicative of a damaged component and the energy within the at least one region excluding the at least one harmonic or sideband series. Moreover, the method includes calculating a damage factor of the component as a function of, at least, the at least one damage ratio. In addition, the method includes comparing the damage factor to a predetermined damage threshold, wherein a damage factor exceeding the predetermined damage threshold is indicative of a damaged component.

In one embodiment, the step of determining the damage ratio(s) based on the energy of at least one harmonic or sideband series within the at least one region indicative of the damaged component and the energy within the at least one region excluding the at least one harmonic or sideband series may include determining an average amplitude of the energy of at least one harmonic or sideband series within the at least one region indicative of the damaged component, determining an average amplitude of the identifying energy within the at least one region excluding the at least one harmonic or sideband series, determining at least one amplitude ratio by dividing the average amplitude of the energy of at least one harmonic or sideband series within the at least one region indicative of the damaged component by the average amplitude of the identifying energy within the at least one region excluding the at least one harmonic or sideband series, and subtracting one from the at least one amplitude ratio to obtain at least one region damage value.

In another embodiment, the method may further include amplifying the amplitude ratio(s) based on a sensitivity factor. For example, in one embodiment, the step of amplifying the amplitude ratio(s) based on the sensitivity factor may include raising the region damage value(s) to an $n^{th}$ power. In further embodiments, the method may include summing a plurality of region damage values, and dividing the sum by a total number of low-energy regions. Further, the method may include identifying the low-energy regions based on kinematic information.

In additional embodiments, the method may further include determining a sum of the energy of the at least one harmonic or sideband series within the at least one region indicative of the damaged component for a plurality of regions of the at least one region. More specifically, in one embodiment, the step of determining the sum of the energy of the at least one harmonic or sideband series within the at least one region indicative of the damaged component for the plurality of regions of the at least one region may include summing an amplitude of each of the plurality of regions, summing the sums of the amplitude from each of the plurality of regions, and amplifying the sum of the sums based on a sensitivity factor.

Accordingly, the step of calculating the damage factor of the component may include multiplying the at least one damage ratio by the sum of the energy of the at least one harmonic or sideband series within the at least one region indicative of the damaged component. In further embodiments, the method may include calculating the damage factor for multiple time periods and trending the damage factor over time.

In several embodiments, the component may include, for example, a gear or a bearing. Further, in certain embodiments, the rotary machine may be a wind turbine.

In another aspect, the present disclosure is directed to a system for detecting damage in a gear of a rotary machine. The system includes one or more sensors for collecting vibration data relating to the gear and a controller communicatively coupled to the one or more sensors. The controller is configured to perform one or more operations, including but not limited to identifying energy of at least one harmonic or sideband series within the at least one region indicative of a damaged gear and identifying energy within the at least one region excluding the at least one harmonic or sideband series. Further, the method includes determining at least one damage ratio based on the energy of at least one harmonic or sideband series within the at least one region indicative of a damaged gear and the energy within the at least one region excluding the at least one harmonic or sideband series. Moreover, the method includes calculating a damage factor of the gear as a function of, at least, the at least one damage ratio. In addition, the method includes comparing the damage factor to a predetermined damage threshold, wherein a damage factor exceeding the predetermined damage threshold is indicative of a damaged gear. It should also be understood that the system may further include any of the additional features and/or steps described herein.

In yet another aspect, the present disclosure is directed to a method for detecting damage in a gear of a wind turbine. The method includes collecting, via one or more sensors, vibration data relating to the gear. The method also includes identifying at least one low-energy region within the vibration data. Further, the method includes identifying energy of at least one harmonic or sideband series within the at least one region indicative of a damaged gear. Moreover, the method includes identifying energy within the at least one region excluding the at least one harmonic or sideband series. The method also includes comparing the energy of at least one harmonic or sideband series within the at least one region indicative of the damaged gear and the energy within the at least one region excluding the at least one harmonic or sideband series. In addition, the method includes calculating a damage factor of the gear based, at least in part, on the comparison. As such, the method includes determining whether damage is present in the gear based on the damage factor. It should also be understood that the method may further include any of the additional features and/or steps described herein.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 7 illustrates a graph of a low-energy region of vibration data of a component without damage according to the present disclosure;

FIG. 8 illustrates a graph of a low-energy region of vibration data of a component with damage according to the present disclosure;

FIG. 9 illustrates a graph of a low-energy region of vibration data of a component, particularly illustrating extracted energy of a damage indication pattern according to the present disclosure;

FIG. 10 illustrates a graph of a low-energy region of vibration data of a component, particularly illustrating remaining energy according to the present disclosure; and FIG. 11 illustrates a plurality of graphs depicting vibration data for a healthy component of a rotary machine, an early-stage damaged component, and a late-stage damaged component according to the present disclosure.

DETAILED DESCRIPTION

Figure 1:
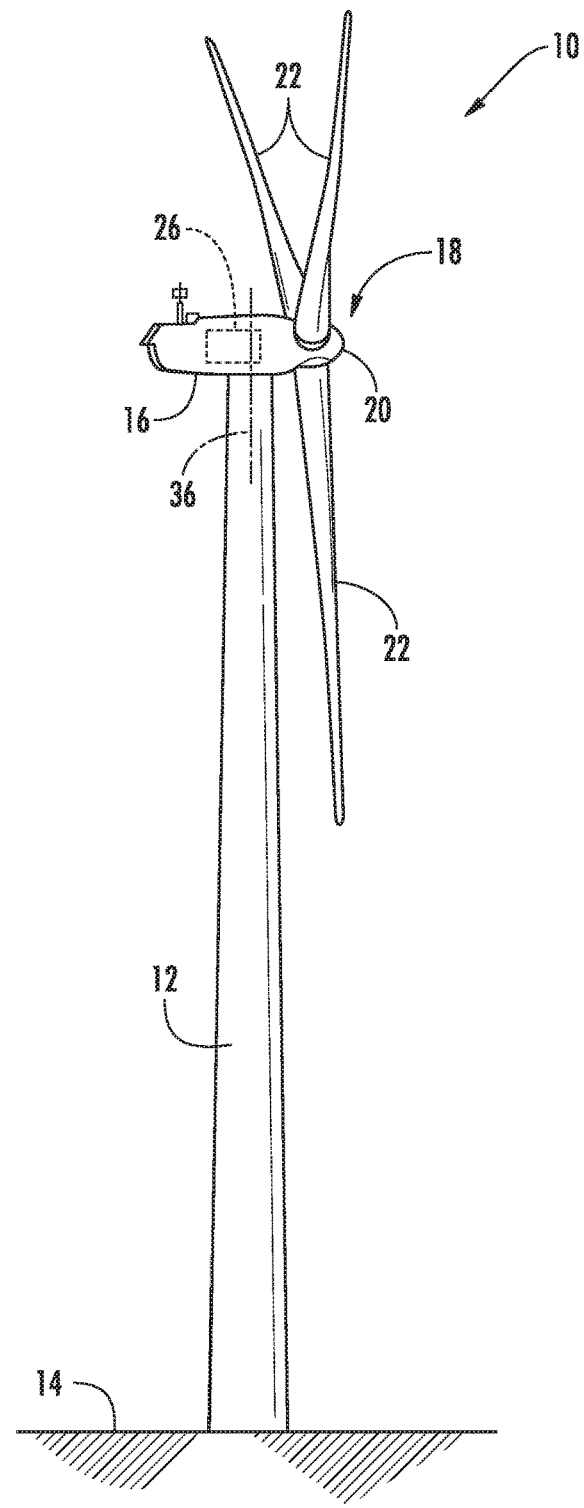
FIG. 1 illustrates a perspective view of a wind turbine according to one embodiment of the present disclosure.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Generally, the present disclosure is directed to systems and methods for detecting damaged components in rotary machines, such as wind turbine, that utilize vibration spectrum data to trend the energy of patterns associated with component damage. More specifically, algorithms of the present disclosure generate a scalar value, or damage factor, which can be trended over time to indicate damage propagation in the components of the rotary machines. For example, for wind turbine gearboxes, the present disclosure detects damage of the planetary stage gears (e.g. the ring gear, planet gears, and sun gear), as well as higher-speed parallel gear stages by lowering the output of healthy components while amplifying the output of damaged components to allow for earliest possible automated threshold detection with minimal false positive events. Such separation between damaged and healthy components allows for lower thresholds to be set to alert technicians of damaged components. Thus, the present disclosure increases machine availability by reducing unplanned downtime, prolonging component life, reducing potential secondary damage, and increasing monitoring efficiency for accurate component damage detection.

Referring now to the drawings, FIG. 1 illustrates a perspective view of one embodiment of a wind turbine 10 according to the present disclosure. Though the present disclosure is described with reference to wind turbines, it should be understood that the systems and methods of the present disclosure may be applicable to any rotary machines (e.g., gas turbines, steam turbines, or any other turbine system for power generation). As shown, the wind turbine 10 includes a tower 12 extending from a support surface 14, a nacelle 16 mounted on the tower 12, and a rotor 18 coupled to the nacelle 16. The rotor 18 includes a rotatable hub 20 and at least one rotor blade 22 coupled to and extending outwardly from the hub 20. For example, in the illustrated embodiment, the rotor 18 includes three rotor blades 22. However, in an alternative embodiment, the rotor 18 may include more or less than three rotor blades 22. Each rotor blade 22 may be spaced about the hub 20 to facilitate rotating the rotor 18 to enable kinetic energy to be transferred from the wind into usable mechanical energy, and subsequently, electrical energy. For instance, the hub 20 may be rotatably coupled to drivetrain system 28 (FIG. 2) positioned within the nacelle 16 to permit electrical energy to be produced.

Figure 2:
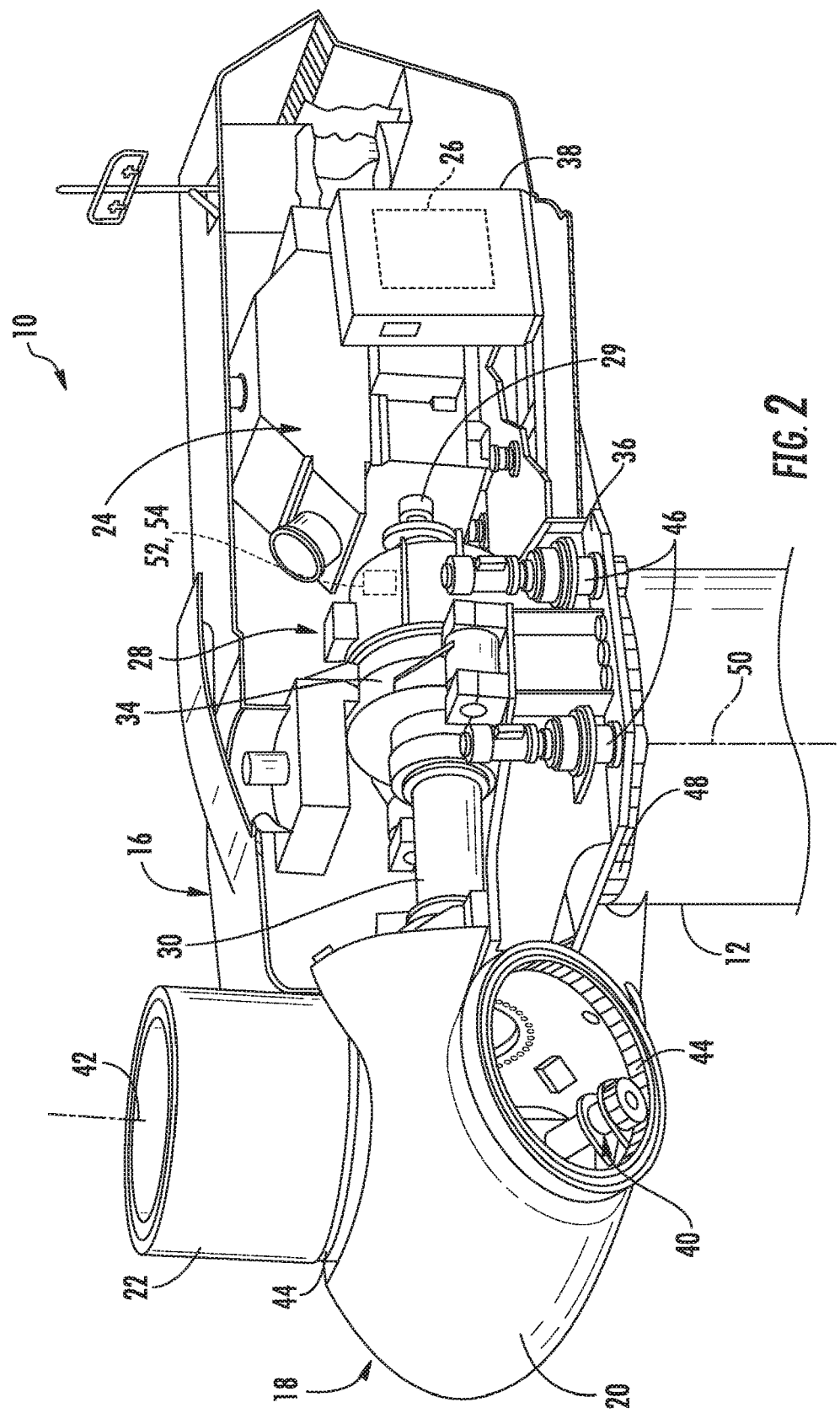
FIG. 2 illustrates a perspective, internal view of a nacelle of a wind turbine according to one embodiment of the present disclosure.

Referring now to FIG. 2, a simplified, internal view of one embodiment of the nacelle 16 of the wind turbine 10 housing the drivetrain system 28 therein is illustrated. As shown, the drivetrain system 28 includes, at least, a generator 24 disposed within the nacelle 16. In general, the generator 24 may be coupled to the rotor 18 of the wind turbine 10 for generating electrical power from the rotational energy generated by the rotor 18. For example, the rotor 18 may include a main shaft 30 coupled to the hub 20 for rotation therewith. The generator 24 may then be coupled to the main shaft 30 such that rotation of the main shaft 30 drives the generator 24. For instance, in the illustrated embodiment, the generator 24 includes a generator shaft 29 rotatably coupled to the main shaft 30 through a gearbox 34. However, in other embodiments, it should be appreciated that the generator shaft 29 may be rotatably coupled directly to the main shaft 30. Alternatively, the generator 24 may be directly rotatably coupled to the main shaft 30. It should be appreciated that the main shaft 30 may generally be supported within the nacelle 16 by a support frame or bedplate 36 positioned atop the wind turbine tower 12.

As shown in FIGS. 1 and 2, the wind turbine 10 may also include a turbine control system or a turbine controller 26 within the nacelle 16. For example, as shown in FIG. 2, the turbine controller 26 is disposed within a control cabinet 38 mounted to a portion of the nacelle 16. However, it should be appreciated that the turbine controller 26 may be disposed at any location on or in the wind turbine 10, at any location on the support surface 14 or generally at any other location. The turbine controller 26 may generally be configured to control the various operating modes (e.g., start-up or shut-down sequences) and/or components of the wind turbine 10.

Each rotor blade 22 may also include a pitch adjustment mechanism 40 configured to rotate each rotor blade 22 about its pitch axis 42 via pitch bearing 44. Similarly, the wind turbine 10 may include one or more yaw drive mechanisms 46 communicatively coupled to the controller 26, with each yaw drive mechanism(s) 46 being configured to change the angle of the nacelle 16 relative to the wind (e.g., by engaging a yaw bearing 48 of the wind turbine 10 to rotate the nacelle 16 about yaw axis 50).

In addition, as shown in FIG. 2, the wind turbine 10 may further include one or more sensors 52, 54 for monitoring various vibrations thereof. For example, as shown, the illustrated sensors 52, 54 may be gearbox sensors configured to monitor vibrations of the gearbox 34 and/or any other components of the drivetrain system 28 so as to detect damage of one or more of the components described herein. As such, the sensors 52, 54 may be any suitable sensor capable of detecting such vibration signals. In addition, it should be understood that the wind turbine 10 may include any suitable number of sensors for detecting such vibrations.

Figure 3:
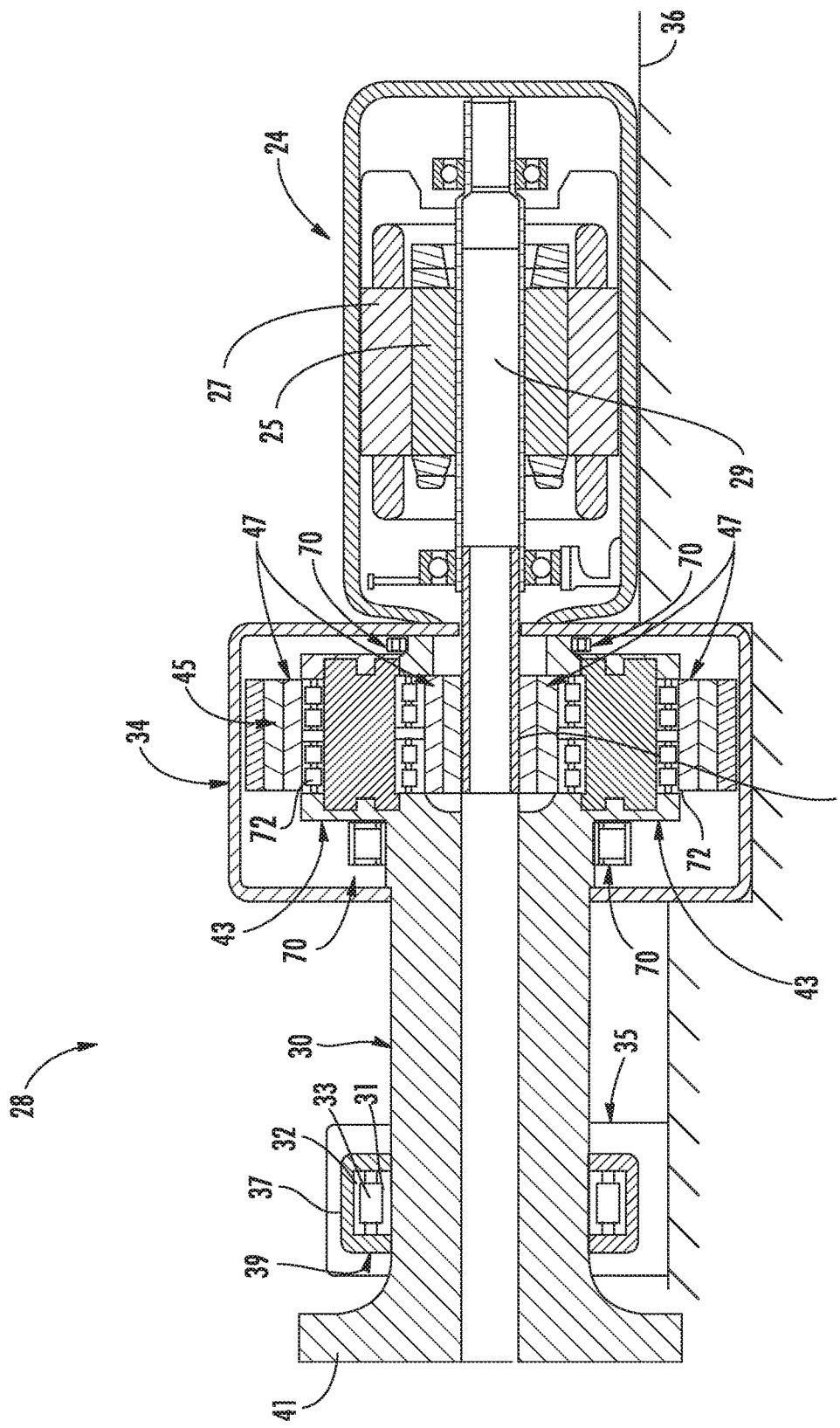
FIG. 3 illustrates a cross-sectional view of one embodiment of a drivetrain system of a wind turbine according to the present disclosure.

Referring now to FIG. 3, a detailed, cross-sectional view of the drivetrain system 28 of the wind turbine 10 is illustrated to further depict the various components thereof. As mentioned, the drivetrain system 28 includes, at least, the generator 24 and the gearbox 34. Further, as shown, the generator 24 includes a generator rotor 25 and a generator stator 27. As is generally known in the art, the generator rotor 25 is a generally movable component of the generator 24, while the stator 27 is a generally stationary component of the generator 24. Further, in certain embodiments, the generator 24 may be a doubly-fed induction generator (DFIG). However, it should be understood that the generator 24 according to the present disclosure is not limited to DFIG generators, and may include any generator suitable for powering the wind turbine 10 of the present disclosure. In general, the rotor blades 16 rotate the generator rotor 25 of the generator 24. As such, the generator rotor 25 may be operably connected to the hub 18. Accordingly, operation of the rotor blades 16 rotates the rotor hub 18, which rotates the generator rotor 25 and thus operates the generator 24.

Further, as shown, the low-speed main shaft 30 is configured to provide an input rotational speed to the gearbox 34. For example, the hub 18 may be mounted to the main shaft 30. As shown, the main shaft 30 may include a main flange 41 configured to engage a mating flange (not shown) on the hub 18 to mount the hub 18 to the main shaft 30. Thus, during operation of the wind turbine 10, the rotational speed of the rotor blades 16 may be directly transmitted through the hub 18 to the main shaft 30 as an input rotational speed.

The main shaft 30 may extend through and be supported by at least one support housing 35 or a plurality of support housings 35. For example, a forward housing 37 and, in some embodiments, an aft housing (not shown), may be provided to support the main shaft 30. In addition, the housings 35 may include one or more bearings 39 configured to interact with the main shaft 30. For example, as shown, the forward housing 37 may include a locating bearing 39 (also referred to herein as a main shaft bearing 39) configured therein, while the aft housing may include a floating bearing (not shown) configured therein. It should be understood that the present disclosure is not limited to locating bearings and floating bearings positioned in housings as described above and the figures are provided for illustrative purposes only. Further, as shown, the main shaft bearing(s) 39 may include an inner race 31, an outer race 32, and a plurality roller elements 33 configured therebetween.

Still referring to FIG. 3, the gearbox 34 as described herein may be a planetary gearbox 34. As such, the gearbox 34 may be configured to convert the input rotational speed from the main shaft 30 to an output rotational speed. In one embodiment, the output rotational speed may be faster than the input rotational speed. Alternatively, however, the output rotational speed may be slower than the input rotational speed. In one embodiment, the gearbox 34 may be a single stage gearbox. Thus, the input rotational speed may be converted to the output rotational speed through a single stage of various mating gears, as discussed below. Alternatively, however, the gearbox 34 may be a multiple stage gearbox, and the input rotational speed may be converted to the output rotational speed through multiple stages of various mating gears.

More specifically, the illustrated embodiment of the planetary gearbox 34 includes a stationary ring gear 45 and a plurality of rotatable gears. As such, the stationary ring gear 45 supports the various rotatable gears configured therein. In addition, the stationary ring gear 45 includes various axes for the rotatable gears to rotate about. In certain embodiments, the planetary gearbox 34 may also include a stationary ring gear 45, one or more rotatable planetary gears 47, and a rotatable sun gear 49. For example, in one embodiment, the planetary gearbox 34 may include four planetary gears 47. However, it should be understood that more or less than four planetary gears 47 are within the scope and spirit of the present disclosure. In addition, each of the rotatable gears in the planetary gearbox 34 includes a plurality of gear teeth (not shown). As such, the teeth may mesh together such that the various gears 45, 47, 49 engage each other.

In several embodiments, the carrier 43 may drive the planetary gearbox 34. Thus, the carrier 43 and the main shaft 30 may be coupled such that the input rotational speed of the main shaft 30 is provided to the carrier 43. For example, a gearbox disk may connect the carrier 43 and main shaft 30, or the carrier 43 and main shaft 30 may be otherwise suitably connected. Alternatively, however, the ring gear 45 or the sun gear 49 may drive the planetary gearbox 34.

Referring still to FIG. 3 and as mentioned, the drivetrain system 28 of the present disclosure may further include an output or generator shaft 29. More specifically, as shown, the generator shaft 29 may be coupled with the gearbox 34, and configured to rotate at the output rotational speed. In particular embodiments, for example, the generator shaft 29 may be the sun gear 49. Thus, the sun gear 49 may engage the planetary gears 47 and may further extend from the planetary gearbox 34 towards the generator 24. In other embodiments, the generator shaft 29 may be coupled to the sun gear 49 or other output gear of the planetary gearbox 34 or other suitable gearbox such that the generator shaft 29 may rotate at the output rotational speed.

In addition, various bearings 39, 70, 72 may surround the various rotatable components of the drivetrain system 28 to facilitate relatively efficient rotation of such rotatable components. For example, as shown, a plurality of carrier bearings 70 may surround the planetary carrier 43 and a plurality of planet bearings 72 may surround the planetary gears 47 and/or additional bearings which support the sun gear or sun gear shaft (not shown). Such bearings 70, 72 may be roller bearings, and include various roller elements arranged in generally annular arrays, or may be journal bearings or any other suitable bearings. In addition, the bearings 39, 70, 72 as described herein may also be referred to as low-speed bearings.

Figure 4:
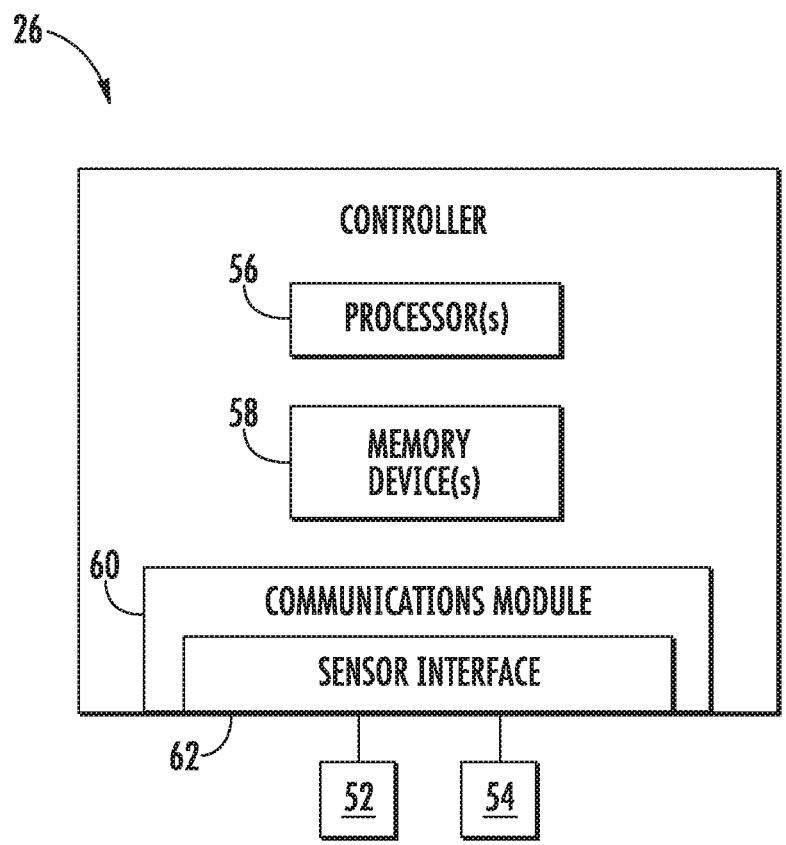
FIG. 4 illustrates a block diagram of one embodiment of suitable components that may be included in a wind turbine controller according to the present disclosure.

Referring now to FIG. 4, there is illustrated a block diagram of one embodiment of suitable components that may be included within the controller 26 (or a separate controller) according to the present disclosure. As shown, the controller 26 may include one or more processor(s) 56 and associated memory device(s) 58 configured to perform a variety of computer-implemented functions (e.g., performing the methods, steps, calculations and the like and storing relevant data as disclosed herein). Additionally, the controller 26 may also include a communications module 60 to facilitate communications between the controller 26 and the various components of the wind turbine 10. Further, the communications module 60 may include a sensor interface 62 (e.g., one or more analog-to-digital converters) to permit signals transmitted from the vibration sensors 52, 54 to be converted into signals that can be understood and processed by the processors 56. It should be appreciated that the sensors 52, 54 may be communicatively coupled to the communications module 64 using any suitable means. For example, as shown in FIG. 4, the sensors 52, 54 are coupled to the sensor interface 62 via a wired connection. However, in other embodiments, the sensors 52, 54 may be coupled to the sensor interface 62 via a wireless connection, such as by using any suitable wireless communications protocol known in the art.

In additional embodiments, the vibration sensors 52, 54 may also be coupled to a separate controller that may or may not be located in the control cabinet 38. As such, the sensors 52, 54 may provide related information to the turbine controller 26 and/or the separate controller. It should also be appreciated that, as used herein, the term "monitor" and variations thereof indicates that the various sensors of the wind turbine 10 may be configured to provide a direct measurement of the parameters being monitored and/or an indirect measurement of such parameters. Thus, the sensors described herein may, for example, be used to generate signals relating to the parameter being monitored, which can then be utilized by the controller 26 to determine the condition.

As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory device(s) 58 may generally comprise memory element(s) including, but not limited to, computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory device(s) 58 may generally be configured to store suitable computer-readable instructions that, when implemented by the processor(s) 56, configure the controller 26 to perform various functions including, but not limited to, transmitting suitable control signals to implement corrective action(s) in response to a distance signal exceeding a predetermined threshold as described herein, as well as various other suitable computer-implemented functions.

Figure 5:
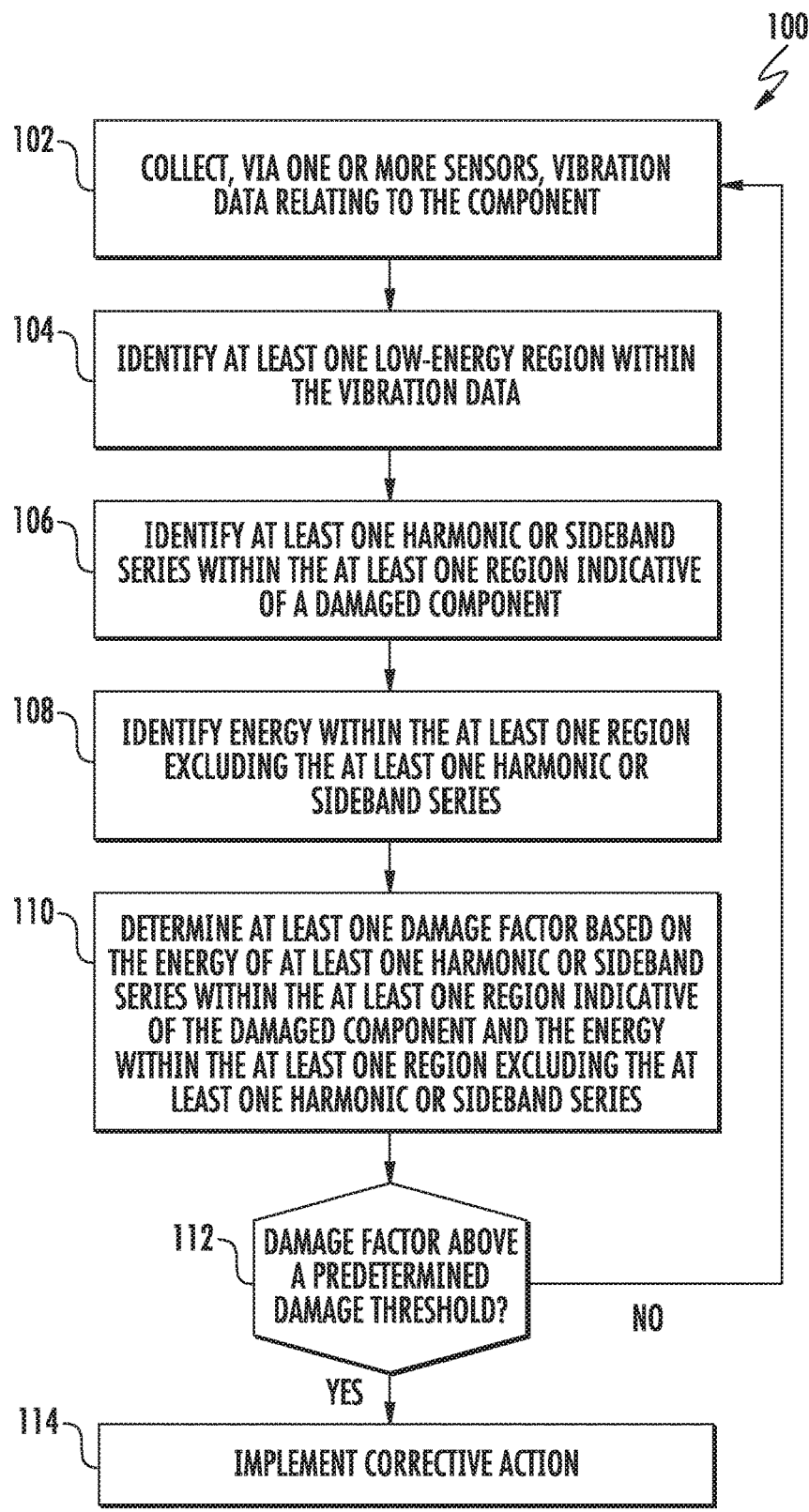
FIG. 5 illustrates a flow diagram of one embodiment of a method for detecting damage in a component of a rotary machine according to the present disclosure.

Referring now to FIG. 5, the turbine controller 26 is further configured to implement an algorithm to detect damage of one or more of the components of the wind turbine 10. For example, in one embodiment, the controller 26 is configured to implement a method 100 for detecting damage in one or more of the gears 45, 47, 49 of the wind turbine 10. Thus, as shown, the system and methods of the present disclosure are designed to lower the output of healthy components while amplifying the output of damaged components to allow for earliest possible automated threshold detection with minimal false positive events.

Figure 6:
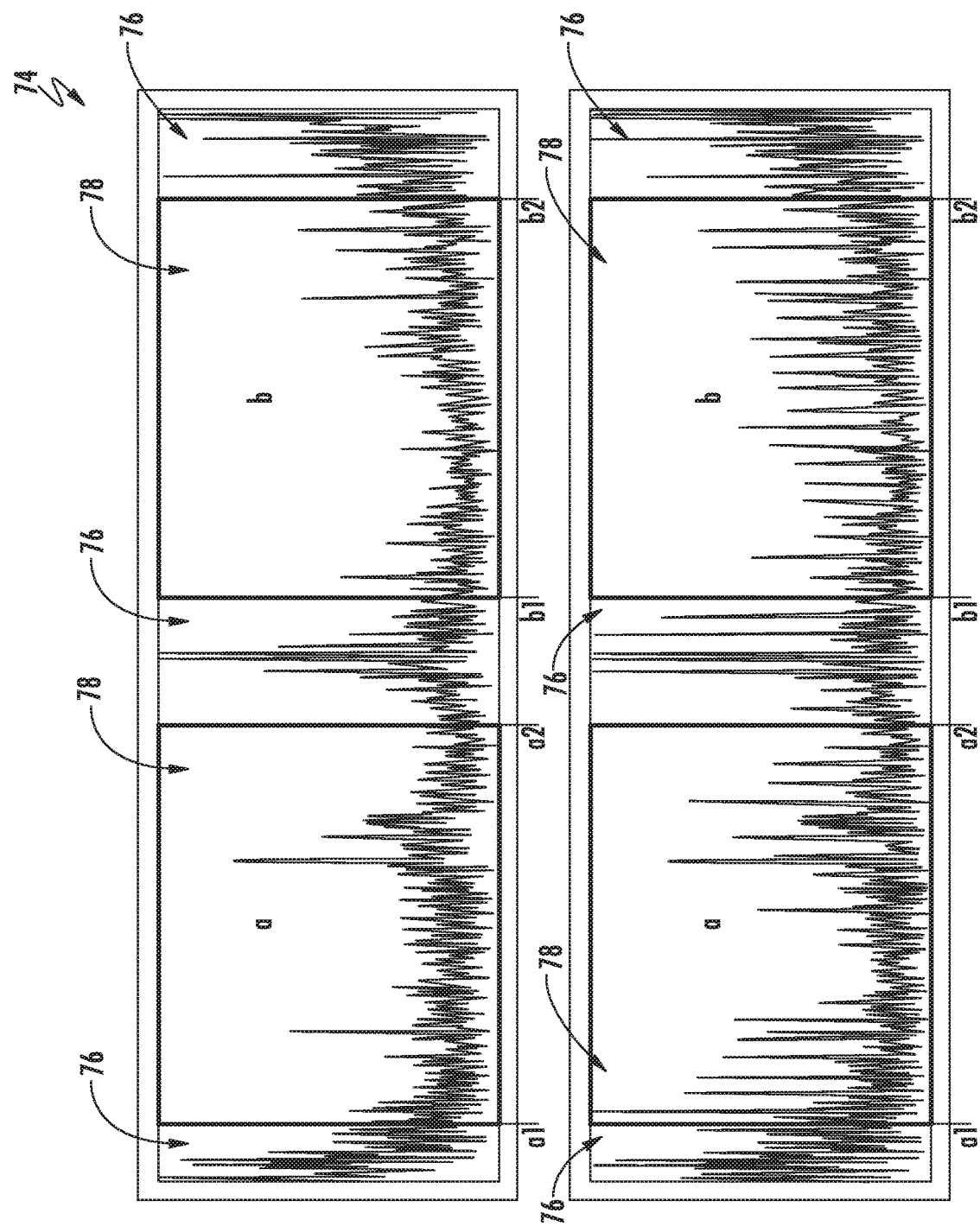
FIG. 6 illustrates a graph of one embodiment of vibration data according to the present disclosure.

As shown at 102, the method 100 includes collecting vibration data 74 relating to the component via the sensors 52, 54. More specifically, as shown in FIG. 6, the turbine controller 26 is configured to collect vibration data 74 relating to the gears 45, 47, 49 via the sensors 52, 54.

Further, as shown, the vibration data 74 may include regions of high energy 76 and regions of low energy 78. Thus, referring back to FIG. 5, as shown at 104, the method 100 includes identifying at least one low-energy region 78 within the vibration data 74. As shown at 106, the method 100 includes identifying energy of at least one harmonic or sideband series within at least one of the low-energy regions 76 of the vibration data 74 indicative of a damaged component, including but not limited to gears (such as gears 45, 47, 49), shafts (such as main shaft 30), and/or bearings 39, 70, 72. Moreover, as shown at 108, the method 100 includes identifying energy within the vibration data 74 excluding the at least one harmonic or sideband series. For example, as shown in FIG. 6, two low-energy regions 78 are identified, i.e. regions a and b. In additional embodiments, it should be understood that any number of regions may be identified including more than two and less than two regions. Further, as shown, the top graph illustrates a healthy component, whereas the bottom graph illustrates a damaged graph. More specifically, as shown in FIG. 7, a low-energy region 78 illustrating vibration data 74 from a healthy component is illustrated. In contrast, as shown in FIG. 8, a low-energy region 78 illustrating vibration data 74 from a damaged component (i.e. containing a sideband or harmonic series also referred to herein as a damage indication pattern 84) is illustrated. More specifically, FIG. 9 illustrates the extracted energy 86 of the damage indication pattern 84 from the low-energy region 78 and FIG. 10 illustrates the low-energy region 78 excluding the extracted energy 86 of the damage indication pattern 84 as indicated by reference character 88.

In addition, the regions of low energy 78 may be identified using kinematic information. Thus, to extract the desired energy of damaged components, the controller 26 is configured to utilize the kinematic information to avoid energy content from components operating normally (i.e. not damaged). Such vibration sources are typically inherent in all gearboxes of this design and are removed from the design factor calculation to allow for separation from healthy and damaged components. The kinematic information as described herein may include any of the following: the number of gear teeth of one or more gears of the gearbox 34, a rotating speed, the number of planet gears of a planetary state of the gearbox 34, a pitch diameter of the bearing 39, 70, 72, a roller-element or ball diameter of the bearing 39, 70, 72, a contact angle of the bearing 39, 70, 72, or combinations thereof.

In addition, the controller 26 may be configured to store the vibration data 74 in the memory device(s) 58. Once the vibration data 74 is collected and optionally stored, as shown at 110, the controller 26 is configured to determine a damage factor based on the presence of a sideband or harmonic series indicative of a failed component, e.g. the damage indication pattern 84, within the low energy region(s) 78 in comparison to the remaining energy 88 within the region(s) excluding the sideband or harmonic series. For example, as shown in FIG. 6, to determine the damage factor, the controller 26 may first determine an average amplitude of the energy of at least one harmonic or sideband series within the vibration data 74 indicative of the damaged gear and an average amplitude of the energy excluding the damage indication pattern 84.

Thus, as shown in Equation (1), the controller 26 can then determine at least one amplitude ratio by dividing the average amplitude of the region(s) of the damage indication pattern 84 by the average amplitude of the energy excluding the damage indication pattern 84.

$$\text{Amplitude } Ratio_a = \frac{f_{avg,dip,a}}{f_{avg,non\text{-}dip,a}} \quad \text{Equation (1)}$$

where $f_{avg,dip,a}$ is the average amplitude of region a of the energy in the damage indication pattern 84, and $f_{avg,non\text{-}dip,a}$ is the average amplitude of region a of the energy excluding the damage indication pattern 84.

Further, as shown in Equation (2) below, the controller 26 may subtract one from each of the amplitude ratios to obtain at least one region damage value. In addition, as shown in Equation (s), the controller may amplify the amplitude ratios based on a sensitivity factor S. For example, as shown, the controller 26 may raise the amplitude ratios to an nth power, such as e.g. 2, 3, 4, and so on.

$$\text{Region Damage Value}_a = (\text{Amplitude Ratio}_a - 1)^S \quad \text{Equation (2)}$$

In addition, the controller 26 may sum a plurality of region damage values and divide the sum by a total number of low-energy regions 78 to calculate the damage ratio. In the illustrated embodiment of FIG. 6, for example, there are two low energy regions 78 labeled a and b, respectively.

$$\text{Damage Ratio} = \frac{\text{Region Damage } Value_a + \text{Region Damage } Value_b}{2} \quad \text{Equation (3)}$$

Referring back to FIG. 5, as shown at 112, the method 100 further includes calculating a damage factor of the component as a function of, at least, the at least one damage ratio. For example, in one embodiment, the controller 26 may determine a sum of the energy of the damage indication pattern(s) 84 for a plurality of regions from the vibration data 74 using Equation (4) below. More specifically, as shown, the controller 26 may determine the sum of the energy of the damage indication pattern 84 by summing an amplitude of each of the plurality of regions of the energy of the damage indication pattern(s) 84, summing the sums of the amplitude from each of the plurality of regions of the energy of the damage indication pattern(s) 84, and amplifying the sum of the sums based on a sensitivity factor S.

$$\text{Sum of Damage Indication Pattern Energy} = (\Sigma_{a1} {}^{a2} f_{i,dip} + \Sigma_{b1} {}^{b2} f_{i,dip})^S \quad \text{Equation (4)}$$

where $f_{i,dip}$ is the amplitude of the vibration data at the location of the damage indication pattern(s) 84 in region a of the energy of the damage indication pattern 84.

Accordingly, the method 100 may calculate the damage factor of the component by multiplying the damage ratio by the sum of the energy of the damage indication pattern(s) 84 energy using Equation (5) below.

$$\text{Damage Factor} = \text{Damage Ratio} * \text{Sum of Damage Indication Pattern Energy} \quad \text{Equation (5)}$$

In addition, the damage factor may be scaled by any suitable factor to produce an output value within an acceptable range, i.e. to further amplify the difference between healthy and damaged components.

Referring still to FIG. 5, as shown at 112, once the damage factor is calculated, the method 100 includes comparing the damage factor to a predetermined damage threshold. A damage factor exceeding the predetermined damage threshold is indicative of a damaged component. Thus, as shown at 114, if the damage factor exceeds the predetermined threshold, then the controller 26 may be implement a corrective action or otherwise indicate that the component is damaged. For example, in certain embodiments, the controller 26 may generate an alarm and/or send an alarm signal to an operator.

In further embodiments, the controller 26 may also be configured to continuously calculate and store the damage factor for multiple time periods. As such, the turbine controller 26 is further configured to trend the damage factor over time. Such trending further separates the damage factor values between healthy and damaged components to allow for automated threshold detection.

Advantages of the present disclosure can be further understood with respect to FIG. 11. More specifically, as shown, the first or top row of vibration data 74 represents a healthy component, the second row of vibration data 74 represents an early damaged component, and the third row of vibration data 74 represents a late damaged component. Component damage increases the damage indication pattern energy through the entire spectrum, therefore, comparing damage indication pattern energy to non-damage indication pattern energy outside of normal operation, high energy regions, provides a larger different between damaged and healthy components of the rotary machine. Thus, as shown, the difference between the average amplitude of the damage indication pattern energy 80 and the average energy of the remaining energy 82 is less for healthy components and increases as the component becomes damaged.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method for detecting damage in a component of a rotary machine, the method comprising:
   collecting, via one or more sensors, vibration data relating to the component;
   identifying at least one low-energy region within the vibration data;
   identifying energy of at least one harmonic or sideband series within the at least one region indicative of a damaged component;
   determining an average amplitude of the energy of at least one harmonic or sideband series within the at least one region indicative of the damaged component;
   identifying energy within the at least one region excluding the at least one harmonic or sideband series;
   determining an average amplitude of the identifying energy within the at least one region excluding the at least one harmonic or sideband series;
   determining at least one amplitude ratio by dividing the average amplitude of the energy of at least one harmonic or sideband series within the at least one region indicative of the damaged component by the average amplitude of the identifying energy within the at least one region excluding the at least one harmonic or sideband series; and,
   subtracting one from the at least one amplitude ratio to obtain at least one region damage value;
   determining at least one damage ratio based on the at least one region damage value;
   calculating a damage factor of the component as a function of, at least, the at least one damage ratio; and,
   comparing the damage factor to a predetermined damage threshold, wherein a damage factor exceeding the predetermined damage threshold is indicative of the damaged component.

2. The method of claim 1, further comprising amplifying the at least one amplitude ratio based on a sensitivity factor.

3. The method of claim 2, wherein amplifying the at least one amplitude ratio based on the sensitivity factor further comprises:
   raising the at least one amplitude ratio to an nth power.

4. The method of claim 1, further comprising:
   summing a plurality of region damage values; and,
   dividing the sum by a total number of low-energy regions.

5. The method of claim 4, further comprising identifying the low-energy regions based on kinematic information.

6. The method of claim 1, further comprising determining a sum of the energy of the at least one harmonic or sideband series within the at least one region indicative of the damaged component for a plurality of regions of the vibration data.

7. The method of claim 6, wherein determining the sum of the energy of the at least one harmonic or sideband series within the at least one region indicative of the damaged component for the plurality of regions of the at least one region further comprises:
   summing an amplitude of each of the plurality of regions;
   summing the sums of the amplitude from each of the plurality of regions; and,
   amplifying the sum of the sums based on a sensitivity factor.

8. The method of claim 6, wherein calculating the damage factor of the component further comprises:
   multiplying the at least one damage ratio by the sum of the energy of the at least one harmonic or sideband series within the at least one region indicative of the damaged component for the plurality of regions of the at least one region.

9. The method of claim 1, further comprising calculating the damage factor for multiple time periods and trending the damage factor over time.

10. The method of claim 1, wherein the component comprises at least one of a gear or a bearing.

11. The method of claim 1, wherein the rotary machine comprises a wind turbine.

12. A system for detecting damage in a gear of a rotary machine, the system comprising:
    one or more sensors for collecting vibration data relating to the gear;
    a controller communicatively coupled to the one or more sensors, the controller configured to perform one or more operations, the one or more operations comprising:
       identifying at least one low-energy region within the at least one region;
       identifying energy of at least one harmonic or sideband series within the at least one region indicative of a damaged gear;

determining an average amplitude of the energy of at least one harmonic or sideband series within the at least one region indicative of the damaged component;

identifying energy within the at least one region excluding the at least one harmonic or sideband series;

determining an average amplitude of the identifying energy within the at least one low-energy region excluding the at least one harmonic or sideband series;

determining at least one amplitude ratio by dividing the average amplitude of the energy of at least one harmonic or sideband series within the at least one region indicative of the damaged component by the average amplitude of the identifying energy within the at least one region excluding the at least one harmonic or sideband series;

subtracting one from the at least one amplitude ratio to obtain at least one low-energy region damage value;

determining at least one damage ratio based on the at least one low-energy region damage value;

calculating a damage factor of the gear as a function of, at least, the at least one damage ratio; and, comparing the damage factor to a predetermined damage threshold, wherein a damage factor exceeding the predetermined damage threshold is indicative of the damaged gear.

13. The system of claim 12, wherein the one or more operations further comprise:
summing a plurality of region damage values; and,
dividing the sum by a total number of low-energy regions.

14. The method of claim 13, wherein the one or more operations further comprise identifying the low-energy regions based on kinematic information.

15. The system of claim 12, wherein the one or more operations further comprise determining a sum of the energy of the at least one harmonic or sideband series within the at least one region indicative of the damaged component for a plurality of regions of the at least one region.

16. The system of claim 15, wherein determining the sum of the energy of the at least one harmonic or sideband series within the at least one region indicative of the damaged component for the plurality of regions of the at least one region further comprises:
summing an amplitude of each of the plurality of regions;
summing the sums of the amplitude from each of the plurality of regions; and,
amplifying the sum of the sums based on a sensitivity factor.

17. The method of claim 15, wherein calculating the damage factor of the component further comprises:
multiplying the at least one damage ratio by the sum of the energy of the at least one harmonic or sideband series within the at least one region indicative of the damaged component for the plurality of regions of the at least one region.

* * * * *